United States Patent [19]
Choh

[11] Patent Number: 6,063,057
[45] Date of Patent: May 16, 2000

[54] SYRINGE APPARATUS ADAPTED FOR USE IN CATHETERIZATION PROCEDURES

[75] Inventor: Richard T. Choh, Waltham, Mass.

[73] Assignee: Medtronic AVE, Inc., Santa Rosa, Calif.

[21] Appl. No.: 09/088,129

[22] Filed: Jun. 1, 1998

[51] Int. Cl.[7] .................................................. A61M 29/00
[52] U.S. Cl. ................. 604/99; 604/97; 604/181
[58] Field of Search ...................... 604/97–100, 208–211, 604/118, 121, 228, 187, 188, 224, 146, 920, 181

[56] References Cited

U.S. PATENT DOCUMENTS

| | | |
|---|---|---|
| 4,370,982 | 2/1983 | Reilly . |
| 4,526,196 | 7/1985 | Pistillo . |
| 4,723,938 | 2/1988 | Goodin et al. . |
| 4,740,205 | 4/1988 | Seltzer . |
| 4,743,230 | 5/1988 | Nordquest ................................. 604/97 |
| 4,838,864 | 6/1989 | Peterson . |
| 5,057,078 | 10/1991 | Foote et al. ................................. 604/99 |
| 5,084,060 | 1/1992 | Freund et al. . |
| 5,163,904 | 11/1992 | Lampropoulos et al. . |
| 5,213,115 | 5/1993 | Zytkovicz et al. . |
| 5,271,527 | 12/1993 | Haber et al. . |
| 5,284,480 | 2/1994 | Porter et al. ................................. 604/97 |
| 5,306,248 | 4/1994 | Barrington ................................. 604/97 |
| 5,318,533 | 6/1994 | Adams et al. . |
| 5,318,534 | 6/1994 | Williams et al. . |
| 5,336,183 | 8/1994 | Greelis et al. ............................. 607/97 |
| 5,449,344 | 9/1995 | Taylor et al. . |
| 5,470,317 | 11/1995 | Cananzey et al. . |
| 5,634,910 | 6/1997 | Kanner et al. . |
| 5,752,935 | 5/1998 | Robinson et al. ........................ 604/97 |

FOREIGN PATENT DOCUMENTS

| | | |
|---|---|---|
| 261686 | 12/1961 | Australia . |
| 0 446 932 A2 | 9/1991 | European Pat. Off. . |
| 0 565 045 A1 | 10/1993 | European Pat. Off. . |
| WO 92/17221 | 10/1992 | WIPO . |

*Primary Examiner*—Corrine McDermott
*Assistant Examiner*—Cris L. Rodriguez
*Attorney, Agent, or Firm*—Sterne, Kessler, Goldstein & Fox P.L.L.C.

[57] ABSTRACT

The invention relates to a syringe device for limiting the pressure of inflation fluid injected into a balloon catheter. The device includes a cylindrical housing having a proximal end and a distal end. A piston is received within and reciprocally movable between the distal end and the proximal end of the housing. A shaft having a proximal end and a distal end is received within an opening at the proximal end of the housing. The distal end of the shaft is coupled to the piston and the proximal end of the shaft is coupled via a slip clutch device to a hand knob. At least a portion of the external surface of the shaft is fitted with a screw thread, which may be selectively engaged with a complementary screw thread fitted either within the opening at the proximal end of the housing or a collar coupled to the housing. When the shaft is in threaded engagement with the housing, the slip clutch enable the transmission of torque from the knob to the shaft to allow the incremental axial movement of piston if the pressure of the medium within the housing is at or below a predetermined maximum allowable value. However, if the pressure of the medium exceeds the predetermined maximum value, the frictional elements within the slip clutch slip relative to each other and prevent the transmission of torque from the knob to the shaft, and thus any further pressurization of the fluid medium.

21 Claims, 4 Drawing Sheets

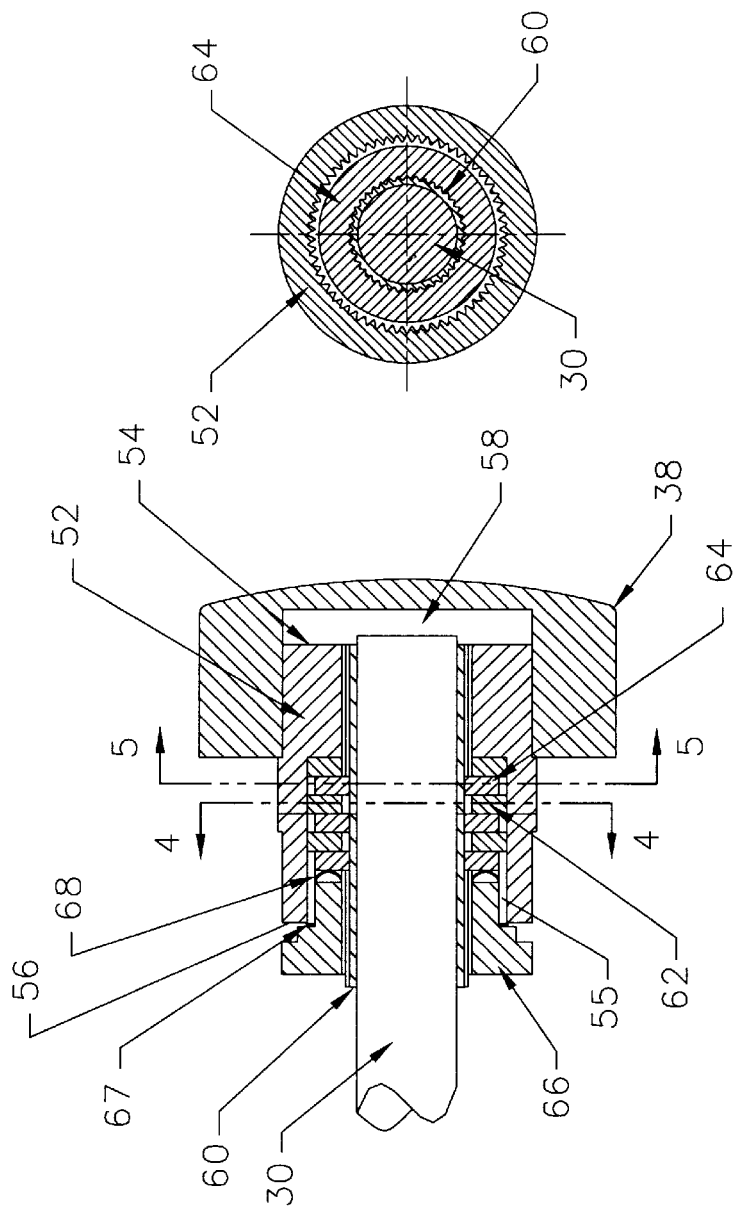

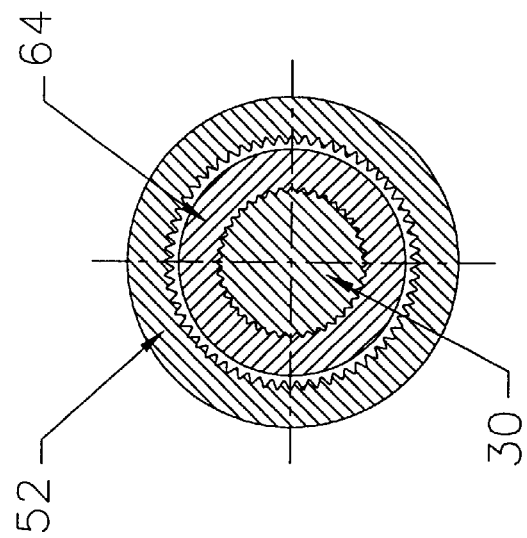
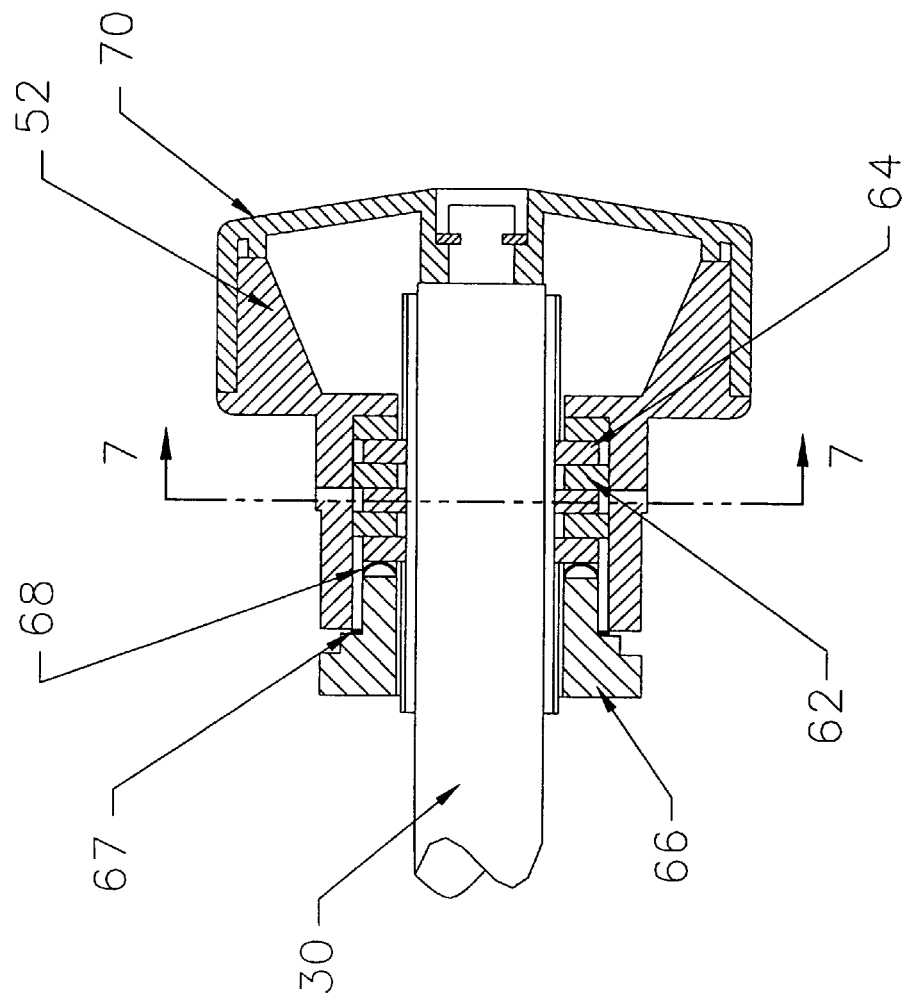
FIG. 7
FIG. 6

SYRINGE APPARATUS ADAPTED FOR USE IN CATHETERIZATION PROCEDURES

FIELD OF INVENTION

The present invention relates to a syringe device used for the delivery of pressurized fluid to balloon catheters. More particularly, the present invention relates to a syringe device adapted to limit the pressure and regulate the flow rate of fluid injected into a balloon catheter.

BACKGROUND OF THE INVENTION

Balloon catheters have been used for many years in a wide range of medical catheterization procedures. Two common balloon catheters designs are angioplasty dilatation balloon catheters and drug delivery balloon catheters. Both of these balloon catheter designs generally comprise an elongated tube having a balloon located at its distal end. The catheter tube includes one or more lumens, which extend longitudinally throughout essentially the entire length of the tube. At least one of the lumens is coupled at its distal end in fluid communication with the interior of the balloon such that it functions as a conduit for the flow of pressurized fluid from the proximal end of the catheter tube to the balloon.

Angioplasty dilatation balloon catheters are used to dilate and open vessels restricted by an atherosclerotic lesion or stenosis. To this end, dilatation balloon catheters include an expandable balloon, which when positioned across the restriction may be inflated with pressurized fluid such that the balloon expands and compresses the stenotic obstruction thereby widening the interior diameter of the vessel. In most cases, it is necessary to perform multiple inflations to sufficiently dilate the restricted vessel. After the dilatation procedure is completed, the balloon is deflated and the catheter is withdrawn from the patient.

Drug delivery balloon catheters are designed to administer therapeutic and/or diagnostic agents to a specific site within the patient's vasculature. Accordingly, drug delivery catheters typically include a perforated balloon which when positioned at the treatment site may be filled with pressurized fluid containing a therapeutic and/or diagnostic agent. When the balloon is sufficiently pressurized with the fluid agent, the fluid migrates through the apertures in the balloon wall and is delivered to the treatment site.

Syringe devices are commonly used by the medical profession for injecting pressurized fluid into either a dilatation balloon catheter or a drug delivery balloon catheter. In its basic form, these syringe devices typically comprise a cylinder and plunger assembly. The cylinder defines an interior chamber having an opening at its proximal end and a fluid conduit at its distal end adapted to be connected in fluid communication to a balloon catheter. The plunger includes a piston movably disposed within the chamber, wherein the piston is connected to the distal end of a shaft which extends through the opening at the proximal end of the cylinder. The plunger further includes a handle connected to the proximal end of the shaft.

In this basic configuration, pressurized fluid contained within the chamber may be forced out of the fluid conduit and into the balloon catheter by manually extending the plunger into the cylinder. Accordingly, the pressure and rate at which the fluid is injected into the balloon catheter depends on the pressure applied on the syringe plunger by the administering physician. It has been found that the precise control of the pressure and rate at which the inflation fluid is injected into the balloon catheter is important, thus requiring great skill on the part of the administering physician. For example, the exertion of excessive pressure on the syringe plunger by the physician may result in over-pressurization of the fluid within the balloon. With regard to a dilatation balloon catheter, such over-pressurization of the fluid within the balloon may cause the balloon to over-inflate to the extent that it exerts excessive pressure on the vessel wall or possibly bursts. With regard to a drug delivery balloon catheter, such over-pressurization may cause high velocity jetting of the fluid through the balloon apertures resulting in possible trauma to the treatment site.

Various syringe devices have been developed for use in catheterization procedures which enable controlled pressurization of the inflation fluid through the incremental movement of the plunger within the cylinder. One design feature commonly implemented involves providing threaded engagement between the plunger shaft and the syringe cylinder. To this end, the plunger shaft is fitted with a screw thread which engages with a complementary screw thread fitted within the opening at the proximal end of the cylinder. According to this design, the plunger may be incrementally advanced within the cylinder by rotating the handle located at the proximal end of the shaft. In addition, similar designs have included pressure gauges for measuring and displaying the pressure of the inflation fluid to the attending physician during the procedure.

Although these designs provide a syringe device which enables the administering physician to more precisely control the pressure and flow rate of the fluid injected into the catheter, they do not offer a mechanism for preventing the over-pressurization of the catheter balloon. Since the pressure and flow rate of the inflation fluid remains dependent on the administering physician, these devices are susceptible to over-pressurization of the catheter balloon through human error. Moreover, it has been found that the use of a pressure gauge to assist the physician in monitoring the pressure at which the inflation fluid is injected into the catheter does not ensure precise control of the infusion of inflation fluid to the catheter balloon. For example, a drop in the pressure indicated on the pressure gauge generally causes the physician to accelerate the movement of the syringe plunger into the syringe barrel, thereby resulting in a pressure spike. Any such pressure spike may result in over-pressurization of the balloon.

Therefore, there exists a need for an apparatus for limiting the pressure and flow rate of the inflation fluid being dispensed from the syringe device to prevent the over-pressurization of the catheter balloon.

OBJECTS AND SUMMARY OF THE INVENTION

In accordance with the present invention, an apparatus is provided for limiting the pressure and flow rate of inflation fluid injected into a balloon catheter. The invention relates to a syringe device having an adjustable rotary slip clutch apparatus for discontinuing the incremental advancement of the plunger within the syringe cylinder when the pressure of the inflation fluid within the syringe reaches a predetermined maximum value.

The apparatus of the present invention includes a cylindrical housing structure comprising a syringe body partially interposed within a barrel. The interior of the syringe body forms a fluid chamber and includes a fluid conduit adapted to its distal end for communication with a balloon catheter. A piston shaft is received within the proximal end of the barrel such that the distal end of the piston shaft extends into the fluid chamber. The piston shaft distal end is connected to a piston, which is slidably movable within the fluid chamber. During inflation of the balloon catheter, the piston is advanced within the fluid chamber toward the distal end of the syringe body. Similarly, the piston may be retracted within the fluid chamber toward the proximal end of the syringe body to withdraw inflation fluid from the catheter and deflate the balloon.

According to a preferred embodiment of the present invention, the piston shaft is adapted to be selectively (1) locked in threaded engagement with the proximal end of the cylinder to enable more precise incremental movement of the piston within the cylinder or (2) unlocked in slidable engagement with the proximal end of the cylinder to permit free axial movement of the piston within the cylinder. The piston shaft includes a handle at its proximal end which may be rotated to effect incremental movement of the piston within the cylinder when the piston shaft is locked in threaded engagement with the cylinder.

The piston shaft further includes a slip clutch mechanism at its proximal end positioned adjacent the handle to prevent the over-pressurization of the balloon catheter during the incremental movement of the piston within the cylinder. In a preferred embodiment, the slip clutch mechanism comprises a driving portion, a driven portion, an annular cavity defined between the driving portion and the driven portion, and friction clutch means disposed within the annular cavity. The friction clutch means includes a plurality of annular elements, at least one of which is mounted to the driving portion for rotation therewith, and at least one of which is mounted to the driven portion for rotation therewith. Means for sealing the annular cavity are provided to prevent foreign material from entering the annular cavity and altering the desired frictional forces of the friction clutch means.

It is, therefore, a principal object of the present invention to provide a syringe device having a slip clutch mechanism coupled to the piston shaft for preventing the over-pressurization of the balloon catheter during the incremental movement of the piston within the cylinder.

It is a further object of the present invention to provide a syringe device for use in balloon catheterization procedures in which the slip clutch mechanism may be adjusted to vary the maximum allowable pressure of the inflation fluid injected into the catheter balloon.

It is a further object of the present invention to provide a syringe device for use in a drug delivery balloon catheter which may be adjusted to vary the maximum allowable pressure for therapeutic and/or diagnostic agents having different fluid characteristics.

Objects and advantages of the invention are set forth in part above and in part below. In addition, these and other objects and advantages of the invention will become apparent herefrom, or may be appreciated by practice with the invention, the same being realized and attained by means of instrumentalities, combinations and methods pointed out in the appended claims. Accordingly, the present invention resides in the novel parts, constructions, arrangements, improvements, methods and steps herein shown and described.

BRIEF DESCRIPTION OF THE DRAWINGS

The present invention consists of the various parts, constructions, arrangements and improvements shown and described. The accompanying drawings which are incorporated in and constitute a part of the specification illustrate embodiments of the invention and together with the description serve to explain the principles of the invention.

FIG. 3 is a longitudinal cross sectional view of the slip clutch assembly of the syringe device shown in FIG. 1;

FIG. 4 is a cross-sectional view of the slip clutch assembly shown in FIG. 3 taken along line 4—4;

FIG. 5 is a cross-sectional view of the slip clutch assembly shown in FIG. 3 taken along line 5—5;

FIG. 6 is a longitudinal cross-sectional view of another embodiment of the slip clutch assembly of the present invention; and FIG. 7 is a cross-sectional view of the slip clutch assembly shown in FIG. 6 taken along line 7—7.

DESCRIPTION OF THE PREFERRED EMBODIMENTS

Referring generally to the embodiments of the invention shown in the accompanying drawings, wherein like reference numbers refer to like parts throughout the various views, the basic principles of the broadest aspects of the invention can be appreciated from FIGS. 1–7.

Figure 1:
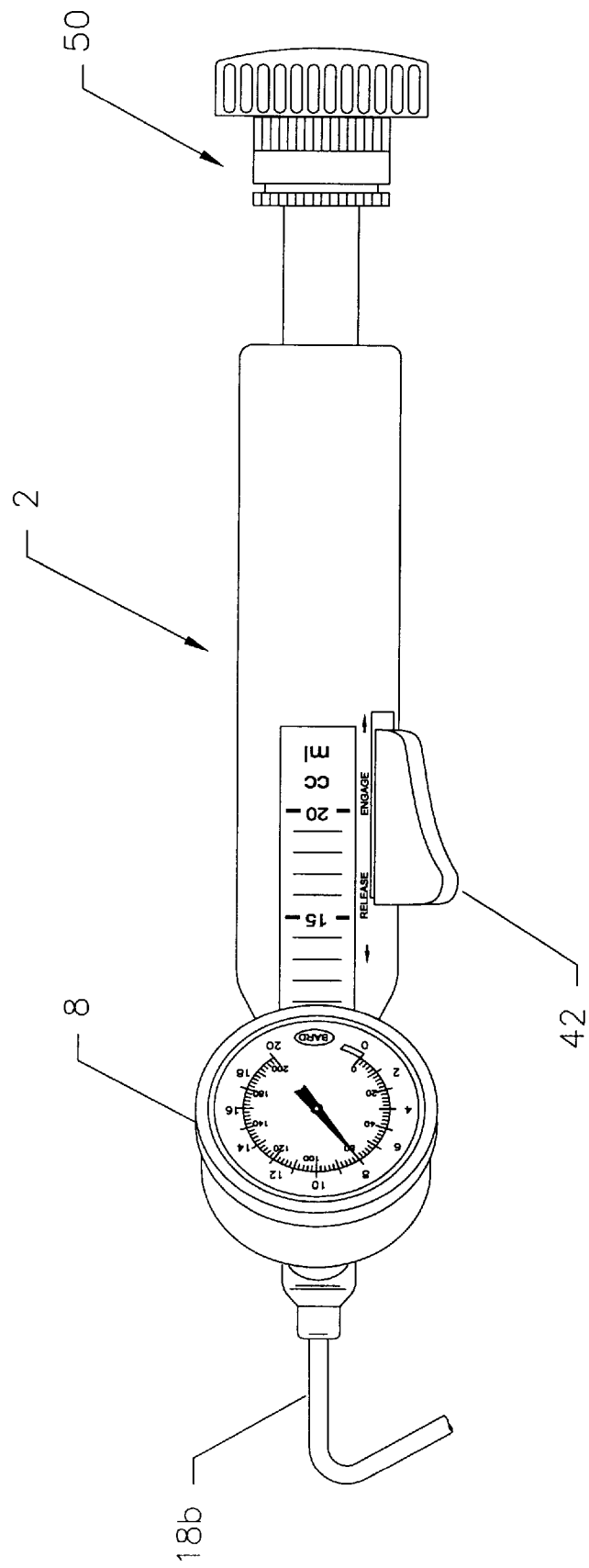
FIG. 1 is a top view of a syringe device in accordance with a preferred embodiment of the present invention.

Referring now to FIG. 1, there is illustrated a syringe device (generally designated as 2) in accordance with a preferred embodiment of the present invention, which may be used with a balloon catheter for angioplasty procedures and the like. Syringe device 2 provides a structure in which a piston shaft may be selectively (1) locked in threaded engagement with the proximal end of the cylinder to enable more precise incremental movement of the piston within the cylinder or (2) unlocked in slidable engagement with the proximal end of the cylinder to permit free axial movement of the piston within the cylinder. As explained in detail below, the syringe device further includes a slip clutch assembly coupled adjacent the proximal end of the piston shaft for preventing the over-pressurization of the balloon catheter by discontinuing the incremental advancement of the piston within the cylinder when the piston shaft is locked in threaded engagement with the cylinder proximal end despite the rotation of the syringe handle by the administering physician.

Figure 2:
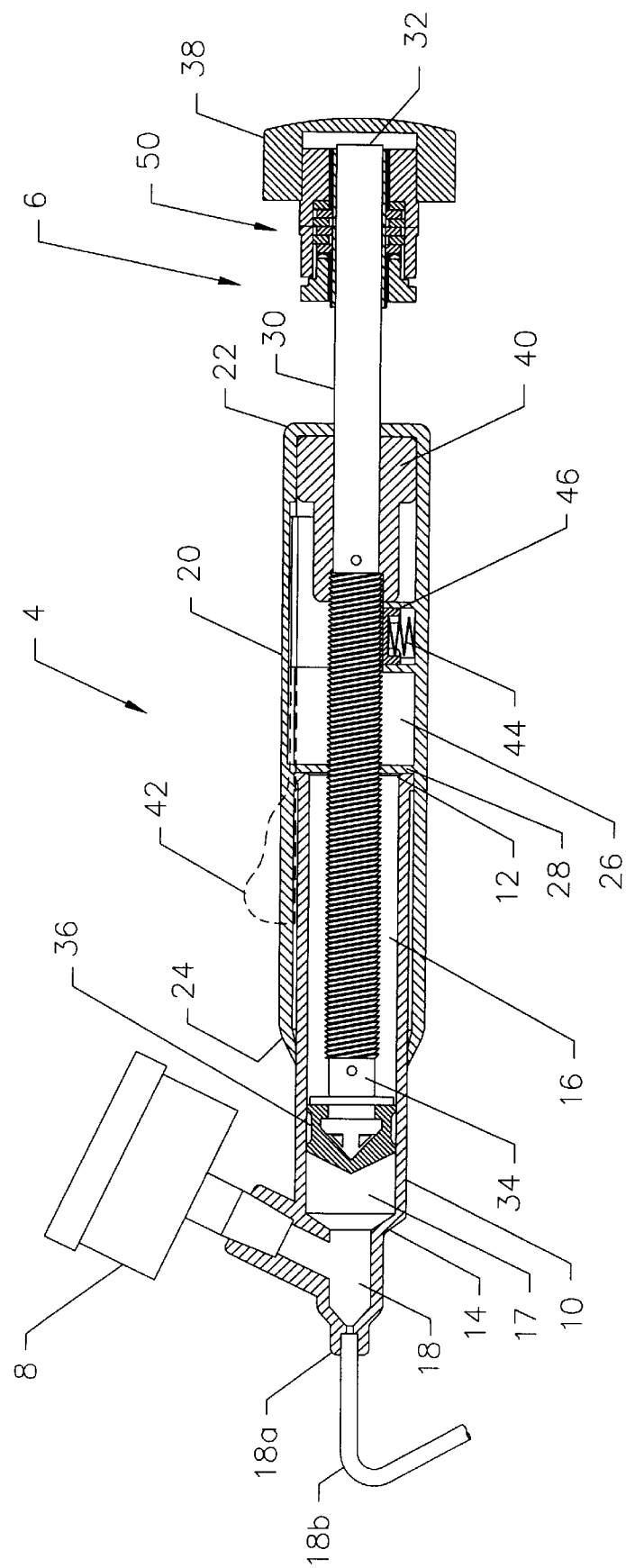
FIG. 2 is a longitudinal cross sectional view of the embodiment of the syringe device shown in FIG. 1.

As shown in FIG. 2, the syringe device of the present invention comprises a housing (generally designated as 4) and a plunger (generally designated as 6). Housing 4 includes an elongated cylindrical syringe body 10 having respective proximal and distal ends 12 and 14, and having a bore extending longitudinally therebetween which defines a syringe chamber 16. The syringe body distal end 14 includes a fluid conduit 18 through which pressurized fluid within syringe chamber 16 may be conveyed to a balloon catheter. Fluid conduit 18 is shaped to form a fitting 18a which may be adapted to receive a catheter or other tube-like device 18b. A pressure gauge 8 is mounted at the distal end of the syringe body 10 and in communication with syringe chamber 16 to indicate the pressure of inflation fluid contained within chamber 16 and passing through fluid conduit 18.

Housing 4 further includes an elongated cylindrical barrel 20 having respective proximal and distal ends 22 and 24. Barrel 20 includes a bore extending longitudinally throughout from proximal end 22 to distal end 24, which defines a chamber 26. Distal end 24 of barrel 20 is adapted to receive the proximal end 12 of syringe body 10. To this end the interior surface of barrel 20 is fitted with an annular flange 28, which abuts the proximal end 12 of syringe body 10.

As further shown in FIG. 2, plunger 6 includes a shaft 30 having respective proximal and distal ends 32 and 34, wherein shaft 30 is received into the proximal end 22 of barrel 20. Shaft 30 is further received into an annular bushing 40 positioned within chamber 26 adjacent the proximal end of barrel 20. Annular bushing 40 functions to stabilize shaft 30 in axial alignment within barrel 20 and syringe body 10. Shaft distal end 34 extends into syringe chamber 16 and is connected to a piston 36 which is reciprocally movable within syringe chamber 16. The outer surface of piston 36 may be formed of an elastomeric material dimensioned to have a cross-sectional area which corresponds with the cross-sectional area of syringe chamber 16 so as to form a fluid tight seal with the chamber side walls. Accordingly, a fluid compartment 17 is formed in a portion of syringe chamber 16 between piston 36 and the distal end 14 of syringe body. Alternatively, piston 36 may have one or more sealing rings mounted about its side wall which engage the interior wall of syringe body 10 to provide a fluid tight seal and prevent fluid from passing around piston 36 as it moves within chamber 16. The proximal end of shaft 30 is coupled to hand knob 38 via an adjustable rotary slip clutch assembly (generally designated as 50). Hand knob 38 is designed to facilitate grasping and rotating the shaft by the user.

According to this arrangement, fluid may be pressurized and injected into a balloon catheter by advancing piston 36 within syringe chamber 16 in a direction toward the distal end of syringe body 10. Similarly, pressurized fluid may be withdrawn from a balloon catheter by retracting piston 36 within syringe chamber 16 in a direction toward the syringe body proximal end 12.

Preferably, plunger 6 and housing 4 are releasably engaged with each other to enable precise incremental movement or free axial movement of piston 36 within syringe chamber 16. To this end, housing 4 preferably includes any of the several locking mechanisms known in the art which allows for selective engagement and disengagement of plunger 6. According to the embodiment shown in FIGS. 1 and 2, such a locking mechanism may comprise a lever 42 operatively coupled to a spring-loaded half nut 46. To enable controlled incremental movement of piston 36 within syringe chamber 16, the outer surface of half nut 46 and at least a portion of the length of shaft 30 are fitted with complementary screw threads.

As shown in FIG. 1, lever 42 is movable between a release position and an engage position. When lever 42 is in the release position, biasing spring 44 is compressed such that half nut 46 moves in an inoperative position, in which the outside surface of half nut 46 is spaced apart from shaft 30. When lever 42 is in the release position, plunger 6 is freely translatable relative to housing 4. Conversely, when lever 42 is in the engage position, half nut 46 is biased by spring 44 in an operative position whereby the screw thread on the outer surface of half nut 46 mates with the complementary screw thread on shaft 30. It will be understood that when shaft 30 and screw nut 46 are in threaded engagement, piston 36 may be slowly advanced or retracted within syringe chamber 16 by rotating hand knob 38.

The slip clutch assembly used in the present invention may be selected from one of many commercially available slip clutch assemblies, such as model no. MSCA-4 sold by Small Parts, Inc. As shown in greater detail in FIG. 3, a preferred embodiment of the present invention employs a rotary slip clutch assembly 50 which comprises a tubular housing 52 having a bore 58 extending from a proximal end 54 to a distal end 56. Housing 52 is fixedly coupled to hand knob 38 such that the rotation of knob 38 is directly translated to housing 52.

Rotary slip clutch 50 further includes a bushing sleeve 60 which is fixedly coupled to the proximal end of shaft 30. As shown in FIG. 3, bushing sleeve 60 is longitudinally disposed within housing 52, forming an annular cavity 55 therebetween. Furthermore, bushing sleeve 60 and housing 52 are coupled by a plurality of friction plates disposed within annular cavity 55. According to the present invention, the clutch assembly is basically comprised of two sets of flat, annular friction plates 62 and 64, respectively. The first set of annular friction plates 62 are fixedly coupled to housing 52. As such, friction plates 62 are mounted for rotation with housing 52, which, in turn, is mounted to hand knob 38 for rotation therewith. The second set of annular plates 64 are fixedly coupled to bushing sleeve 60. Accordingly, friction plates 64 are mounted for rotation with bushing sleeve 60, which, in turn, is mounted to shaft 30 for rotation therewith. In this respect, housing 52 may be described as a driving element which transmits torque to shaft 30, a driven element, via the frictional engagement of annular friction plates 62 and 64. As illustrated in FIGS. 4 and 5, friction plates 62 and 64 may be fixedly coupled to housing 52 and bushing 60, respectively, by means of interlocking gear teeth.

Referring now to FIG. 3, first and second sets of friction plates 62 and 64 are alternately disposed in a series along the longitudinal axis of bushing sleeve 60 and housing 52. Thus, with exception of the outside surfaces of the first and last friction plates in the series, the side surface of each friction plate 62 is positioned adjacent the side surface a friction plate 64.

A torque adjustment ring 66 and wave spring washer 68 are provided to enable adjustment of the frictional forces between the contacting side surfaces of sets of friction plates 62 and 64. As illustrated in FIG. 3, torque adjustment ring 66 is movably coupled to the inside surface at the distal end of housing 52. In the preferred embodiment of the present invention, housing 52 and torque adjustment ring 66 are movably coupled through the engagement of complementary screw threads fitted on the outside surface of torque adjustment ring 66 and the inside surface of housing 52. In addition, wave spring washer 68 is disposed adjacent the distal end of torque adjustment ring 66. To this end, the frictional force between the contacting side surfaces of sets of friction plates 62 and 64 may be adjusted by varying the longitudinal position of torque adjustment ring 66 to either increase or decrease the uniform compressive force exerted by wave spring washer 68 on friction plates 62 and 64. Adjustment ring 66 may also include a sealing ring 67, which provides sealing engagement between adjustment ring 66 and housing 52 to prevent any foreign material from entering annular cavity 55. It will be understood that any such foreign material may affect the desired frictional forces between the contacting side surfaces of friction plates 62 and 64.

Alternately, slip clutch assembly 50 may be integrally constructed with shaft 30 and configured to form all or part of the grasping handle. For example, as shown in FIG. 6, housing 52 may be configured to include a flange portion which functions with cap 70 to form a grasping handle. Further, friction plates 64 may be fixedly coupled directly to the outside surface of shaft 30. As shown in FIG. 7, friction plates 64 may be fixedly coupled to shaft 30 by means of interlocking gear teeth.

In operation, a syringe device 2 loaded with inflation fluid in compartment 17 is coupled to a balloon catheter (not shown). The balloon catheter is coupled in fluid communication with conduit 18 positioned at the distal end of syringe body 10.

According to the preferred embodiment, the administering physician initially has lever 42 in the release position such that shaft 30 in the disengaged or unlocked state and piston 36 may freely move within syringe chamber 16. In this unlocked state, the physician moves the shaft 30 and piston 36 axially forward within syringe chamber 16 toward syringe body distal end 14 to moderately pressurize the inflation fluid.

The physician then typically locks shaft 30 in threaded engagement with half nut 46 by moving lever 42 to the engage position to enable more controlled pressurization of the inflation fluid. In the locked state, the physician may incrementally advance piston 36 toward the syringe body distal end 14 to further pressurize the inflation fluid injected from compartment 17 to the balloon catheter by rotating handle 38 and transmitting torque to shaft 30 via the frictional engagement of plates 62 and 64.

As the physician rotates shaft 30 and advances piston 36 within syringe chamber 16, the pressure of the inflation fluid within compartment 17 steadily increases. The pressurization of the inflation fluid, in turn, produces an opposing reaction force on piston 36 and shaft 30. When shaft 30 is locked in threaded engagement with half nut 46, this opposing reaction force is converted to a torque acting opposite the torque applied by the physician in rotating handle 38 to advance piston 36 within syringe chamber 16. Thus, as the pressure of the inflation fluid within compartment 17 increases, the counteracting torque on shaft 30 increases. When the counteracting torque on shaft 30 increases and exceeds the frictional force between the side surfaces of plates 62 and 64, plates 62 and 64 will slip relative to each other, thereby discontinuing the transmission of any torque applied by the physician in rotating handle 38. It will be understood that by presetting the frictional force between the side surfaces of plates 62 and 64 at a value which corresponds to the intended maximum pressure for the inflation fluid, the friction plates will slip relative to each other such that the pressure of the inflation fluid within compartment 17 cannot exceed the maximum pressure. Consequently, any further torque applied by the physician in rotating handle 38 will not be transmitted to shaft 30 to advance piston 36 within syringe chamber 16. Only after the pressure of the inflation fluid decreases to a value at or below the maximum pressure value will plates 62 and 64 frictionally engage and further transmit any torque applied at handle 38.

While only a few embodiments have been illustrated and described in connection with the present invention, various modifications and changes in the apparatus will become apparent to those skilled in the art. For example, while the present invention has been described above with reference to a syringe device having a two-component housing and a feature for enabling selective engagement/disengagement of the shaft, the basic aspects of the present invention can be adapted for use with any syringe device enabling incremental axial movement of a piston within a fluid chamber by rotation of the piston shaft. All such modifications or changes falling within the scope of the claims are intended to be included therein.

I claim:

1. An inflation/deflation syringe device for use with a balloon catheter, comprising:

(a) a cylinder having a proximal end, a distal end and a fluid conduit proximate the distal end of the cylinder adapted for communication with a balloon catheter;

(b) a shaft received within the proximal end of the cylinder, the shaft having a proximal end and a distal end;

(c) a piston disposed within the cylinder and coupled to the distal end of the shaft, the piston being movable in one direction during inflation and in a second direction during deflation of the balloon catheter;

(d) a locking mechanism for engaging the shaft within the cylinder to affect incremental axial movement of the piston within the cylinder by rotation of the shaft to enable controlled pressurization or depressurization of medium contained within the cylinder;

(e) a slip clutch coupled to the shaft for enabling the transmission of torque to the shaft when the pressure of the medium within the cylinder is at or below a maximum allowable pressure and discontinuing the transmission of torque to the shaft when the pressure of the medium within the cylinder exceeds a maximum allowable pressure.

2. The inflation/deflation syringe device of claim 1, wherein the slip clutch comprises:

(a) a first annular member coupled concentrically about the external surface of the shaft for rotation therewith;

(b) a second annular member wherein the first annular member is concentrically disposed within the second annular member and defines an annular cavity therebetween;

(c) a friction clutch disposed within the annular cavity for enabling the transmission of torque from the second annular member to the shaft when the pressure of the medium within the cylinder is at or below a maximum allowable pressure or discontinuing the transmission of torque from the second annular member to the shaft when the pressure of the medium within the cylinder exceeds a maximum allowable pressure.

3. The inflation/deflation syringe of claim 2, wherein the friction clutch comprises a plurality of friction elements having a generally annular disk shape, at least one of the friction elements is coupled to the first annular member for rotation therewith and at least one other of the friction elements is coupled to the second annular member for rotation therewith, wherein the side surface of at least one friction element coupled to the first annular member is positioned adjacent the side surface of at least one friction element coupled to the second annular member for frictional engagement therewith.

4. The inflation/deflation syringe device of claim 3, wherein the friction clutch further includes an adjustment means for selectively increasing or decreasing the frictional force between the friction elements coupled to the first and second annular members.

5. The inflation/deflation syringe device of claim 4, wherein the adjustment means comprises:

(a) an annular ring disposed within the annular cavity; and (b) biasing means operably positioned adjacent the annular ring to engage the plurality of friction elements, whereby the annular ring may be selectively positioned to increase or decrease the axial force exerted by the biasing means on the plurality of friction elements so as to vary the frictional force between adjacent surfaces of the plurality of friction elements.

6. The inflation/deflation syringe device of claim 5, wherein the annular ring includes screw threads fitted on at least a portion of its external surface which are dimensioned to mate with screw threads fitted on at least a portion of the internal surface of the first annular member to enable the selective positioning of the annular ring within the annular cavity.

7. The inflation/deflation syringe device of claim 6, wherein the biasing means comprises a wave spring washer.

8. The inflation/deflation syringe device of claim 2, wherein the slip clutch further comprises means for sealing the annular cavity to prevent foreign material from entering the annular cavity.

9. The inflation/deflation syringe device of claim 2, wherein the slip clutch further comprises a knob coupled to the second annular member for facilitating rotation of the second annular member.

10. The inflation/deflation syringe device of claim 1, wherein at least a portion of the length of the shaft is fitted with a screw thread designed for engagement with a complementary screw thread fitted on the locking mechanism to enable incremental axial movement of the piston within the cylinder.

11. The inflation/deflation syringe device of claim 1, further comprising a knob coupled to the slip clutch for facilitating the transmission of torque to the shaft when the pressure of the medium within the cylinder is at or below a maximum allowable pressure value.

12. The inflation/deflation syringe device of claim 1, wherein the slip clutch comprises:
   (a) a driven element coupled to the shaft for rotation therewith;
   (b) a driving element that is configured to transfer applied torque to said driven element, wherein the driven element and the driving element form an annular cavity therebetween;
   (c) a friction clutch comprising first and second sets of annular shaped disks, wherein the disks are dimensioned to be positioned concentric to the shaft within the annular cavity with the first set of disks being coupled to the driving element for rotation therewith and the second set of disks being coupled to the driven element for rotation therewith;
   (d) an annular ring disposed within the annular cavity; and
   (e) biasing means operably positioned adjacent the annular ring to engage the first and second sets of disks, whereby the annular ring may be selectively positioned within the annular cavity to increase or decrease the axial force exerted by the biasing means on the disks so as to vary the frictional force between adjacent surfaces of the disks.

13. The inflation/deflation syringe device of claim 12, wherein the annular ring includes screw threads fitted on at least a portion of its external surface which mate with screw threads fitted on at least a portion of the internal surface of the first annular member to enable the selective positioning of the annular ring within the annular cavity.

14. The inflation/deflation syringe device of claim 12, wherein the biasing means comprises a wave spring washer.

15. The inflation/deflation syringe device of claim 12, wherein the slip clutch further comprises means for sealing the annular cavity to prevent foreign material from entering the annular cavity.

16. A selectively controllable inflation/deflation syringe device for use with a balloon catheter, comprising:
   (a) a cylinder having a proximal end, a distal end and a fluid conduit proximate the distal end of the cylinder adapted for communication with a balloon catheter;
   (b) a shaft received within the proximal end of the cylinder, the shaft having a proximal end and a distal end;
   (c) a piston disposed within the cylinder and coupled to the distal end of the shaft, the piston being movable in one direction during inflation and in a second direction during deflation of the balloon catheter;
   (d) means for selectively engaging the shaft with the cylinder to enable incremental axial movement of the piston within the cylinder by rotation of the shaft or disengaging the shaft within the cylinder to enable free axial movement of the piston within the cylinder;
   (e) a slip clutch coupled to the shaft for enabling the transmission of torque to the shaft when the shaft is selectively engaged with the cylinder to provide for incremental axial movement of the piston within the cylinder and the pressure of the medium within the cylinder is at or below a maximum allowable pressure, but discontinuing the transmission of torque to the shaft when the shaft is selectively engaged with the cylinder and the pressure of the medium within the cylinder exceeds a maximum allowable pressure.

17. The selectively controllable inflation/deflation syringe device of claim 16, wherein the slip clutch comprises:
   (a) a first annular member coupled concentrically about the external surface of the shaft for rotation therewith;
   (b) a second annular member wherein the first annular member is concentrically disposed within the second annular member and defines an annular cavity therebetween;
   (c) a friction clutch disposed within the annular cavity for enabling the transmission of torque from the second annular member to the shaft when the pressure of the medium within the cylinder is at or below a maximum allowable pressure or discontinuing the transmission of torque from the second annular member to the shaft when the pressure of the medium within the cylinder exceeds a maximum allowable pressure.

18. The selectively controllable inflation/deflation syringe of claim 17, wherein the friction clutch comprises a plurality of friction elements having a generally annular disk shape, at least one of the friction elements is coupled to the first annular member for rotation therewith, and at least one other of the friction elements is coupled to the second annular member for rotation therewith, wherein the side surface of at least one friction element coupled to the first annular member is positioned adjacent the side surface of at least one friction element coupled to the second annular member for frictional engagement therewith.

19. The selectively controllable inflation/deflation syringe device of claim 16, wherein at least a portion of the length of the shaft is fitted with a screw thread designed for engagement with a complementary screw thread fitted on the engaging/disengaging means to enable incremental axial movement of the piston within the cylinder.

20. The selectively controllable inflation/deflation syringe device of claim 16, further comprising a knob coupled to the slip clutch for facilitating the transmission of torque to the shaft when the pressure of the medium within the cylinder is at or below a maximum allowable pressure value.

21. The selectively controllable inflation/deflation syringe device of claim 16, wherein the cylinder comprises:
   (a) a syringe body having a proximal end, a distal end and a bore extending from the proximal end to the distal end, wherein the bore defines a syringe chamber,
   (b) a barrel having a proximal end, a distal end and a bore extending throughout its length from the proximal end to the distal end, wherein the bore defines a barrel chamber and the distal end of the barrel receives the proximal end of the syringe body such that at least a portion of the length of the syringe body is encompassed within the barrel chamber; and
   (c) a fluid conduit formed at the distal end of the syringe body adapted for communication with a balloon catheter.

* * * * *